United States Patent
Benco et al.

(10) Patent No.: US 6,746,595 B2
(45) Date of Patent: Jun. 8, 2004

(54) AMMONIUM IONOPHORE, AN AMMONIUM ION SELECTIVE MATRIX, AN AMMONIUM ION-SELECTIVE SENSOR, AND A METHOD FOR DETECTING AMMONIUM IONS IN A FLUID SAMPLE

(75) Inventors: John S. Benco, Medfield, MA (US); W. Grant McGimpsey, Worcester, MA (US)

(73) Assignees: Bayer Corporation, East Walpole, MA (US); Worcester Polytechnic Institute, Worcester, MA (US)

( * ) Notice: Subject to any disclaimer, the term of this patent is extended or adjusted under 35 U.S.C. 154(b) by 33 days.

(21) Appl. No.: 10/040,665

(22) Filed: Jan. 7, 2002

(65) Prior Publication Data

US 2003/0159948 A1 Aug. 28, 2003

(51) Int. Cl.$^7$ .................... G01N 27/333; C07D 245/00; C07D 273/00; B01D 36/16
(52) U.S. Cl. .................... 205/789.5; 204/418; 540/470; 540/474; 540/450; 210/500.28; 210/500.38
(58) Field of Search ................. 540/450, 470, 540/474; 210/500.27, 500.28, 500.33, 500.37; 204/416, 418, 403.05, 415; 205/778, 789, 789.5

(56) References Cited

FOREIGN PATENT DOCUMENTS

JP  61-88134  * 5/1986

OTHER PUBLICATIONS

JPO abstract of JP 61088134 A (Senda et al.).*
CAPLUS abstract of JP 61088134 A2 9Senda et al.).*
Ovchinnikov et al. ("Physicochemcial basis of the functioning of biological membranes. Dynamic conformational properties of enniatin B and its potasium ion complex in solution," Biochemcial and Biophysical Research Communications (1969), 37(4), 668–76).*
Billich et al. ("N–Methyltransferase function of the multifunctional enzyme enniatin synthetase," Biochemistry (1987), 26(25), 8417–23).*
Chemical structure of enniatin B from File Registry in the STN database.*
Bakker E. et al. *Chem. Rev.* 97: 3083–3132 (1997).
Bodanszky, M., *Principles of Peptide Synthesis*, pp. 233–260 (Springer–Verlag, Berlin, 1984).
Bradshaw, J.S. et al., *Comprehensive Supramolecular Chemistry*; Lehn, J.M. et al. Ed., vol. 1, pp. 64–65 (Pergammon, New York, 1996).
Casnati A. et al., *Chem. Eur. J.* 2: 436–445 (1996).
*Catalog and Peptide Synthesis Handbook* (Calbiochem-Novabiochem Corp. San Diego, California, 2000).
March J., *Advanced Organic Chemistry* 4 ed.(John Wiley and Sons, New York, 1992).

* cited by examiner

Primary Examiner—Alex Noguerola

(57) ABSTRACT

An ammonium selective ionophore for use in ion selective electrodes.

12 Claims, 1 Drawing Sheet

AMMONIUM IONOPHORE, AN AMMONIUM ION SELECTIVE MATRIX, AN AMMONIUM ION-SELECTIVE SENSOR, AND A METHOD FOR DETECTING AMMONIUM IONS IN A FLUID SAMPLE

FIELD OF THE INVENTION

The invention relates generally to the detection of ions by ion selective compounds. More particularly, the invention relates to the detection of ammonium ions.

BACKGROUND OF THE INVENTION

Many receptor molecules (called "ionophores") are capable of binding the ammonium cation. The ionophore nonactin has been widely used in ion selective electrodes (ISE) for the determination of ammonium ions in biological fluid samples.

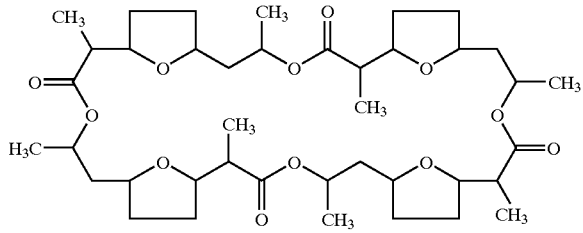

However, nonactin has poor selectivity for ammonium ions over potassium ions. Also, nonactin is relatively expensive.

Thus, there is a need in the art for ionophores with superior or at least comparable selectivity for ammonium to that of nonactin, but which are not as cost prohibitive.

SUMMARY OF THE INVENTION

The invention provides an ammonium ion selective matrix or ion selective electrode (ISE) containing as an ionophore a compound having the following general structure (I):

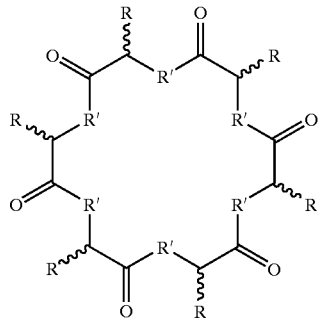

where (a) R is independently or in combination hydrogen or a alkyl, alkoxyalkyl, alkoxyacyl, alkylamino, alkylnitroso, alkylcyano, alkylthio, alkylsulfinyl, alkylsulfonyl, alkenyl, alkoxyalkenyl, alkenylacyl, alkenylamino, alkenylnitroso, alkenylcyano, alkenylthio, alkenylsulfinyl, alkylsulfonyl, alkynyl, alkoxyalkynyl, alkynylacyl, alkynylamino, alkynylnitroso, alkynylcyano, alkynylthio, alkynylsulfinyl, alkynylsulfonyl, and substituted or unsubstituted aryl groups with or with out heteroatoms; and (b) R' is either nitrogen or oxygen. Other suitable groups and further descriptions of the groups described here can be determined by one of skill in the art by reference to an organic chemistry textbook (for example, Bruice P Y, *Organic Chemistry, Third Edition* (Prentice-Hall, 2001) or Wade L W, *Organic Chemistry, Fourth Edition*, (Prentice-Hall, 1999)). Isomers of ionophore I of different stereo configurations can be included in the ion selective matrix or electrode of the invention. The ionophore used in the matrix or electrode of the invention has superior or at least comparable ammonium ion selectivity to that of nonactin. Advantageously, the ionophore is easier and less expensive to produce than nonactin.

The invention also provides methods of making and using an ion selective matrix or electrode containing ionophore I.

The invention also provides a compound having the following structure (II):

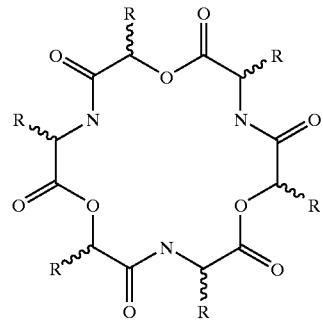

where R is hydrogen or a alkyl, alkoxyalkyl, alkoxyacyl, alkylamino, alkylnitroso, alkylcyano, alkylthio, alkylsulfinyl, alkylsulfonyl, alkenyl, alkoxyalkenyl, alkenylacyl, alkenylamino, alkenylnitroso, alkenylcyano, alkenylthio, alkenylsulfinyl, alkylsulfonyl, alkynyl, alkoxyalkynyl, alkynylacyl, alkynylamino, alkynylnitroso, alkynylcyano, alkynylthio, alkynylsulfinyl, and alkynylsulfonyl groups and substituted or unsubstituted aryl groups with or with out heteroatoms. All isomers having a difference in stereo configuration are included in the scope of the compound of the invention. The compound of the invention (compound II) may usefully be included as an ionophore in the ammonium ion selective electrode of the invention.

In a particular embodiment, the compound of the invention has the following structure (1).

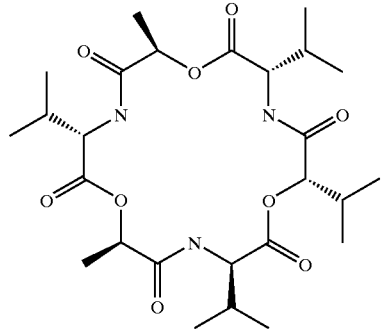

The invention also provides a useful method for synthesizing the compound of the invention from block compounds. This method works especially well when the compound II contains ester linkages and the blocks containing ester linkages within compound II are first synthesized in solution, thus making easier the use of solid phase synthesis.

The following structure is used to illustrate and generalize the method.

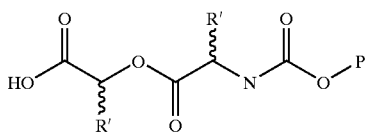

where R' is independently or in combination hydrogen or an alkyl, alkoxyalkyl, alkoxyacyl, alkylamino, alkylnitroso, alkylcyano, alkylthio, alkylsulfinyl, alkylsulfonyl, alkenyl, alkoxyalkenyl, alkenylacyl, alkenylamino, alkenylnitroso, alkenylcyano, alkenylthio, alkenylsulfinyl, alkylsulfonyl, alkynyl, alkoxyalkynyl, alkynylacyl, alkynylamino, alkynylnitroso, alkynylcyano, alkynylthio, alkynylsulfinyl, alkynylsulfonyl, and substituted or unsubstituted aryl groups with or with out heteroatoms. P is any protection group that can be employed which is compatible to the particular solid phase resin in use. Examples of protection groups are the well known Fmoc, Z, Boc, Trt and the like which can be found in any commercial catalog for peptide synthesis such as *Catalog and Peptide Synthesis Handbook* (Calbiochem-Novabiochem Corp; San Diego, Calif.).

In one embodiment, compound 1 can be synthesized from the block compounds B1 and B2:

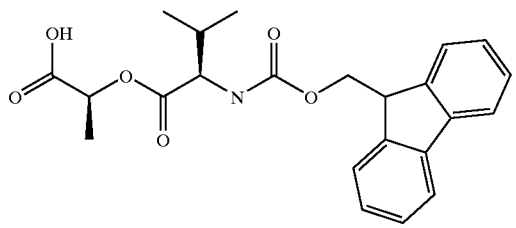

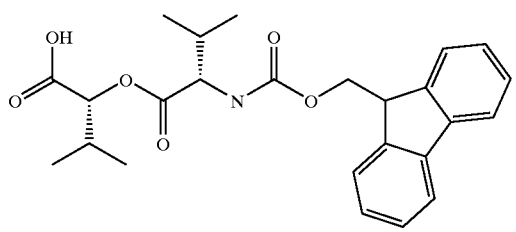

DETAILED DESCRIPTION OF THE INVENTION

Figure 1:
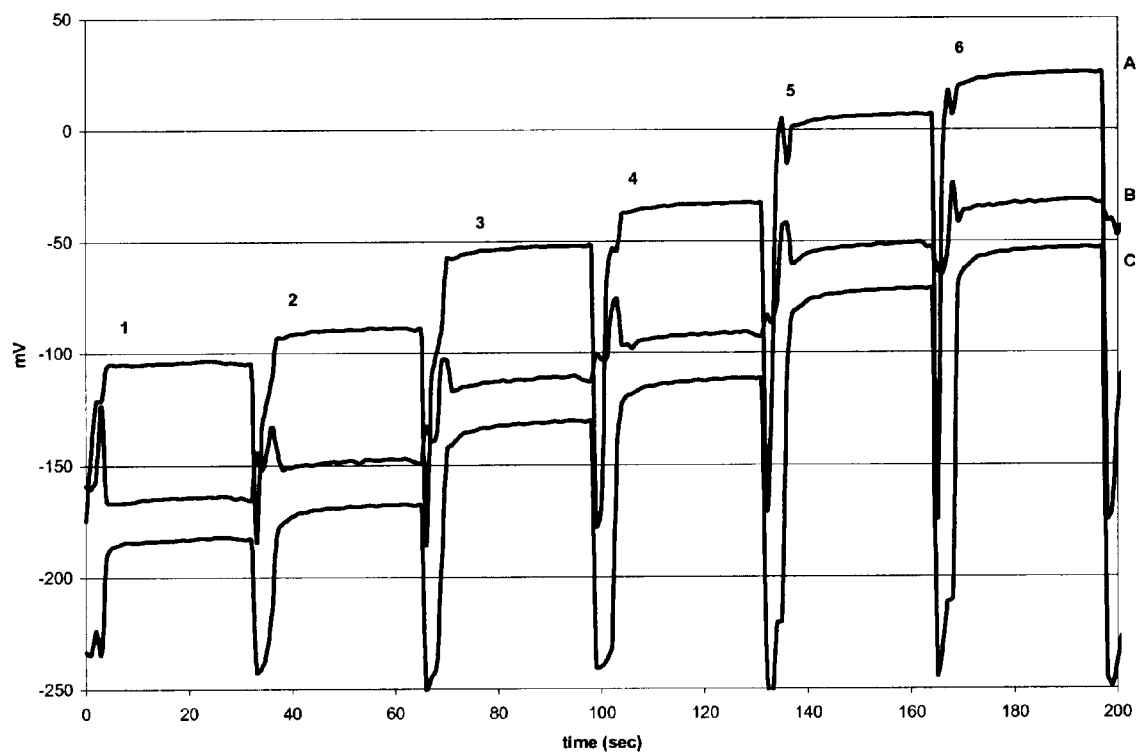
FIG. 1 is a measurement of ammonium concentration over time using an ammonium-selective electrode containing the ionophore of the invention. Three sensors were constructed in a planar format, using compound 1 in an internal electrolyte polymeric layer. The ion selective membrane was composed of 30 wt % polyvinyl chloride, 69 wt % dioctyl phthalate and 1 wt % of 1. The sensors were tested using solutions containing $NH_4Cl$ (0.5–100 mM), 100 mM Tris buffer and 0.05g/l Brij 700. The output of the sensors, measured in mV, are plotted with respect to time. In the FIG., 1=0.05 mM, 2=1 mM, 3=5 mM, 4=10 mM, 5=50 mM, 6=100 mM $NH_4Cl$, respectively, and A, B, and C are sensors #1, #2, and #3, respectively.

The invention provides compositions of matter of the class of compound II described above, which are useful as ionophores for selectively detecting and measuring ammonium ion concentrations. The basis of the utility is an ammonium selective response due to the selective complexing of the ammonium ion by the lipophilic compound of the invention.

Certain cyclohexapeptides have been described in U.S. Pat. No. 6,080,719. However these have not been shown to have ionophoric activity. Rather, they have been used to inhibit the binding of interleukin-4 to the interleukin-4 receptor. Thus, these cyclohexapeptides have only been shown to be suitable for the therapy, prophylaxis and diagnosis of allergies and infections, such as viral, bacterial, parasitic and fungal diseases.

Also provided is a method of synthesizing the compounds from block compounds. In one embodiment, the block compounds are used to synthesize a linear depsipeptide (see, U.S. Pat. Nos. 6,080,719, 6,146,853 and 6,211,145), which is then circularized to form the compound of the invention.

Furthermore, the invention provides ion selective matrices and ion selective electrodes (ISE), for the detection and measurement of ammonium ions in a fluid sample. Ion selective electrodes of the invention can be solid state membrane electrodes, glass membrane electrodes, liquid membrane electrodes having charged ion selective agents, and neutral liquid membrane electrodes having membranes formed from an organic solution containing an electrically neutral, ion selective agent such as an ionophore held in an inert polymer matrix. Solid state ion selective electrodes use a solid membrane as a sensing element or electrode, the membrane being highly selective to ammonium ions and reacting to the ammonium ions with changes in ionic conductivity. The desired ammonium ion selectivity is achieved by incorporating into the ion selective electrode an ionophore of the class of compound I. Ion selective electrodes may further contain an internal reference electrode.

Ion selective matrices can be formed from a matrix material in which an ionophore of the class of compound I is dispersed. The matrix material, whether formed as a support or membrane for the ionophore, can be made, for example, from a plastic material, for example polycarbonate or acrylic sheeting, mineral materials or glass and can have any desired shape, for example plates, cylinders, tubes, tapes or fibers. A particular convenient method is in a planar format (U.S. Pat. No. 5,554,272, for example). The thickness of the coating on the support can be, for example, from 0.01 to 100 μm, preferably from 0.1 to 50 μm, more preferably from 0.1 to 30 μm, and particularly preferably from 0.1 to 10 μm.

U.S. Pat. Nos. 4,995,960, 5,607,567 and 5,531,870 disclose ion selective electrodes that use polymer matrix membranes that include a variety of different ionophores. Other suitable polymer matrix materials are known to the person skilled in the art of making ion selective electrodes. See, e.g., Rundle C C, *A Beginners Guide to Ion selective Electrode Measurements* (Nico2000 Ltd, London, UK., Nov. 9, 2001). The polymers can be selected, for example, from the group consisting of polyolefins, polyesters, polyamides, polyethers, polyimides, polyesteramides, polyamideimides, polyurethanes, polyetherurethanes, polyesterurethanes, polyureas, polyurethaneureas and polysiloxanes, it being possible for the polymers to contain ionizable, basic groups (for example amino groups) or ionizable, acidic groups (for example carboxyl or sulfonyl groups), which may be used as replacement for a counterion of lipophilic salts and can provide improved ion transport. The polymers expediently have a mean molecular weight of at least 5,000, preferably at least 10,000 and particularly preferably at least 20,000 daltons, for example from 20,000 to 200,000 daltons. The polymers preferably have an adequate solubility in organic solvents so that they can be mixed with the other components and can be converted into coatings by conventional coating methods. Alternatively, useful matrices of the invention including hydrophobic binder materials, an ionophore of the class of compound I, and solvating solvents can be prepared using known film-coating or casting or screen printing techniques. Useful plasticizers for this method of making matrices of the invention include, dioctyl phthalate, 2-ethyl hexyl adipate or dioctyl sebacate.

Furthermore, the matrix materials are permeable to ammonium ions. The glass transition temperature of polymers for making the matrices are preferably from −130 to 0° C. The dielectric constant of the polymers is preferably from 2 to 25, particularly preferably from 5 to 15, at 100 Hz and room temperature. The glass transition temperature can be adjusted, for example, by means of the polarity and the chain length and content of structural units.

In one embodiment, the ionophore is covalently attached to the matrix material. In another embodiment, the matrix material contains an ionic additive. For example, the ionic additive can be tridodecylmethylammonium chloride, tetradecylmethylammonium chloride, or other lipophilic salts. In yet another embodiment, an internal reference electrolyte can be separated from the internal reference electrode (e.g., Ag/AgCl) by a salt bridge or, alternatively, graphite can be used as internal reference electrode (see, U.S. Pat. No. 5,554,272, incorporated by reference; see also, U.S. Pat. No. 6,126,801).

Testing of an ionophore in an ISE is well known in the art and may take many forms see, e.g. *Ion Selective Electrode Methodology*, Vol. 1, Covington, A. K., ed., (CRC Press, Inc., 1979) pp. 32–33.

In the health care field, particularly in the area of clinical diagnostics, ion selective electrodes are commonly used to measure the activity or concentration of various ions and metabolites present in fluid samples, especially biological samples. By "biological sample" is meant any fluid of biological origin, including fluids of biological origin which have been chemically or physically treated, diluted, or concentrated prior to analysis. Examples of biological samples include serum, urine, plasma, whole blood, cerebrospinal fluid, amniotic fluid, saliva and tears.

Measurements using ion selective matrices or electrodes of the invention use potentiometric or amperiometric electrochemical processes, which generate potential or current signals that are related to the activity of ammonium ion in a sample. Generally, the signal generated within the matrix or electrode is linearly dependent on the logarithm of the activity of the ammonium ion for potentiometric analyses which follows the well known Nernst equation. The activity of ammonium ion is defined as its concentration multiplied by an activity coefficient, where the activity coefficient is generally known or is available in the art. See, e.g., Rundle C C, *A Beginners Guide to Ion selective Electrode Measurements* (Nico2000 Ltd, London, UK, Nov. 9, 2001).

In operation, one surface of the ion selective matrix or electrode of the invention is immersed in a fluid sample suspected of containing ammonium ions. An ammonium ion-dependent potential develops across the ion selective matrix or electrode at the interface of the solution and the ion selective matrix or electrode. In a potentiometric sensor, this potential varies with the concentration of ammonium ions in solution and its magnitude is measured as a voltage. By comparing the voltage generated at the sensing membrane surface with that generated by a reference electrode using a reference ionic solution, one of skill in the art can calculate the ammonium ion concentration. Sensing instruments for the measurement of electrical output from ion selective electrodes are known in the art and are commercially available.

The details of one or more embodiments of the invention are set forth in the accompanying description. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate the preferred embodiments of the invention. These EXAMPLES should in no way be construed as limiting the scope of the invention, as defined by the appended claims.

EXAMPLE 1

Synthesis of a Compound of the Invention

The synthesis of compound 1 can be carried out in a number of ways. A particularly convenient method known to those of skill in the art is through solid phase synthesis (SPS). See, Zaragoza Dörwald F, *Organic Synthesis on Solid Phase* (Wiley-VCH, Weinheim, 2000). This method works especially well when blocks containing ester linkages within compound 1 are synthesized first in solution. Specifically one synthesizes the following two block compounds (B1 and B2):

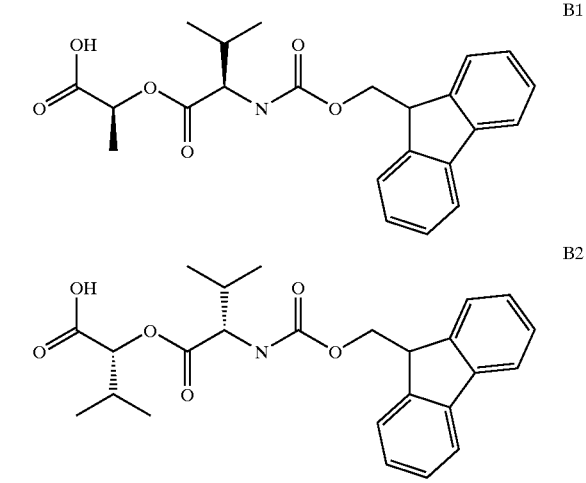

Synthesis of Block Compound B1: Synthesis began with the production of Benzyl ester L-lactic acid (C1):

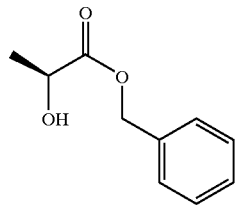

10 g(111 mmol) of L-Lactic acid was dissolved in 150 ml of anhydrous benzyl alcohol. The solution was saturated with HCl gas and stirred for 18 hr where upon the solution was diluted with 200 ml dichloromethane (DCM). The organic layer was washed 3 times with 100 ml 1N KOH, and then with 100 ml 10% citric acid and dried over $Na_2SO_4$. The DCM was then removed under vacuum, 40° C. The benzyl alcohol was removed by vacuum distillation (2.5 mmHg) and the product recovered as a colorless oil at 120° C., 10.3 g, yield 51.3%.

Measurements of the produced C1 were as follows: $^1$H-NMR (400 MHz, $CDCl_3$), δ1.47 (s, 3H), 3.05 (s, 1H), 4.33–4.59 (m, 1H), 5.24 (s, 2H), 7.39 (m, 5H).

Benzyl ester L-lactic-D-Valine-N-fmoc (C2) was produced as follows:

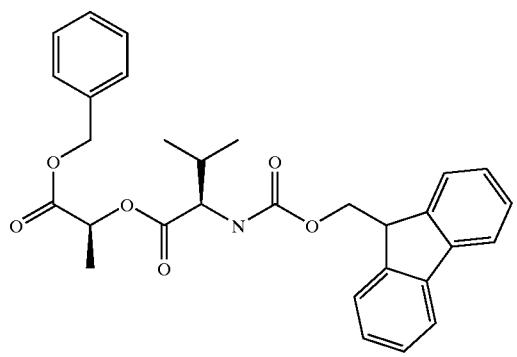

19.4 g (57.2 mmol) of D-Valine-N-fmoc was dissolved in 175 ml of DCM to which 8.92 ml (1 eq.) of diisopropyl-carbodiimide was added. The solution was stirred for 25 min. where upon 10.3 g (1 eq.) of the formed benzyl ester L-lactic acid and 0.696 g (0.1 eq) of 4-dimethylaminopyridine was added. This mixture was then stirred for an additional 18 hr. The insoluble urea thus formed was filtered off and the solution was washed once with 100 ml of water, thrice with 100 ml saturated $NaHCO_3$, thrice with 100 ml 10% citric acid and then dried over $Na_2SO_4$. The DCM was then removed under vacuum, 40° C. to yield a yellow gum. The product was obtained by fractional recrystallization using cold ether to yield 22.6 of a white solid, yield 79%.

Measurements of the produced C2 were as follows: $^1$H-NMR (400 MHz, $CDCl_3$), δ0.92 (d, 3H), 0.99 (d, 3H), 1.53 (s, 3H), 2.25 (m, 1H) 4.22 (m, 1H), 4.39 (m, 1H), 5.17 (s, 2H), 5.33 (d, 1H), 7.29–7.94 (Ar, 13H). $^{13}$C-NMR (400 MHz, $CDCl_3$), δ16.9 ($CH_3$), 17.3 ($CH_3$), 47.1 (CH), 59.0 ($CH_2$), 67.1 (CH), 69.0 (CH), 120.0, 125.1, 127.

Also, for the produced C2, MS-EIS 502.2 (M+H$^+$), 524.4 (M+Na$^+$), 540.2 (M+K$^+$).

The block compound L-Lactic acid-D-valine-N-fmoc (B1) was produced as follows:

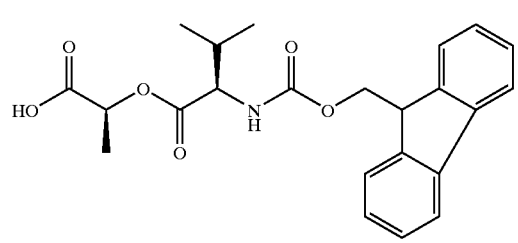

22.6 g (45 mmol) of the formed Benzyl ester L-lactic-D-valine-N-fmoc was dissolved in 150 ml DCM. The benzyl ester group was removed by using 2 g of Pd activated carbon, 10 wt %, and $H_2$ at atmospheric pressure over 3 hr. The spent catalyst was filtered off and the solution was washed thrice with 100 ml saturated $NaHCO_3$. The aqueous phase was acidified with 3N HCl and extracted with DCM. The organic layer was washed with 100 ml brine, dried over $Na_2SO_4$ and concentrated totally under vacuum, 40° C., to afford in quantitative yield the title compound as a white crystalline solid, 18.5 g.

Measurements of the produced B1 were as follows: $^1$H-NMR (400 MHz, $CDCl_3$), δ0.92 (d, 3H), 0.99 (d, 3H), 1.53 (d, 3H), 2.25 (m, 1H), 4.22 (m, 1H), 4.39 (m, 3H), 5.17 (m, 2H) 5.33 (d, 1H), 7.29–7.94 (Ar, 8H). $^{13}$C-NMR (400 MHz, $CDCl_3$), δ16.9 ($CH_3$), 17.5 ($CH_3$), 19.0 ($CH_3$), 47.0 (CH), 59.0 ($CH_2$). 67.1 (CH), 69.0 (CH), 120.0, 124.9, 125.1, 127.1, 127.7, 141.3, 143.7, 143.8 (Ar), 156.4, 171.3, 174.4 (C=O).

Also, for the produced B1, MS-EIS 434.2 (M+Na$^+$), 456.2 (M+K$^+$).

Synthesis of Block Compound B2: Synthesis of B2 began with the production of Benzyl ester D-hydroxisovaleric acid (C3):

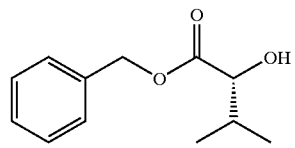

This compound was prepared in same manner as benzyl ester L-lactic acid (above) using 19.5 g (139 mmol) of D-hydroxyisovaleric acid to yield 29.0 g, yield 84.4%.

Measurements of the produced C3 were as follows: $^1$H-NMR (400 MHz, $CDCl_3$), δ0.82 (d, 6H), 0.99 (d, 6H), 2.07 (m, 1H), 2.92 (d, 1H), 4.08 (m, 1H), 5.24 (s, 2H), 7.39 (m, 5H).

Benzyl ester D-hydroxisovaleric-L-valine-N-fmoc (C4) was produced as follows:

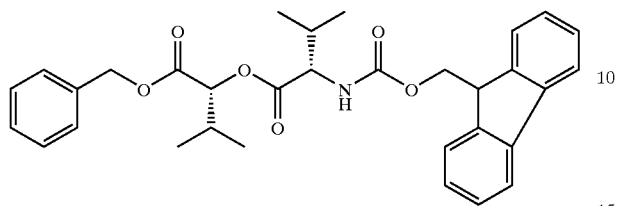

C4

24.0 g (70.7 mmol) of L-valine-N-fmoc, 14.5 g (1 eq.) of the formed Benzyl ester D-hydroxisovaleric acid, 36.2 g (1 eq.) Pybop, 9.5 g (1 eq.) HOBT and 25 ml (2 eq.) of diisopropylethylamine were added to 200 ml DCM. This mixture was then stirred for 4 hr. After such time the solution was washed thrice with 100 ml saturated NaHCO$_3$, thrice with 100 ml 1N HCl acid and then dried over Na$_2$SO$_4$. The DCM was then removed under vacuum, 40° C. The product was obtained by flash chromatography (Biotage Flash40column 15 cm×7 cm, hexane/DCM/EtOAc 60/35/5) to yield 19.0 g of a colorless oil, yield 51.5%.

Measurements of the produced C4 were as follows: $^1$H-NMR (400 MHz, CDCl$_3$), δ0.92–1.01 (m, 12H), 2.26 (m, 2H), 4.23 (m, 1H), 4.38–4.44 (m, 3H), 4.92 (d, 1H), 5.17–5.29 (m, 3H), 7.29–7.78 (Ar, 13H). $^{13}$C-NMR (400 MHz, CDCl$_3$), δ17.0, 17.4, 18.9, 19.1 (CH$_3$), 30.0, 31.1 (CH), 47.1 (CH), 59.2 (CH$_2$), 67.2 (CH$_2$), 120.0, 124.0, 125.1, 127.0, 127.7, 128.4, 128.4, 128.6, 135.1, 141.3, 143.8, 143.9 (Ar), 156.1, 169.0, 171.6 (C=O).

Also, for the produced C4, MS-EIS 552.2 (M+Na$^+$), 568.2 (M+K$^+$).

D-Hydroxyisovaleric acid-L-valine-N-fmoc (B2) was produced as follows:

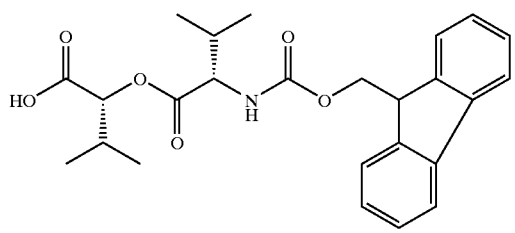

B2

14.5 g (27 mmol) was dissolved in 100 ml DCM. The benzyl ester group was removed by using 2 g of Pd activated carbon, 10 wt %, and H$_2$ at atmospheric pressure over 2 hr. The spent catalyst was filtered off and the solution was washed thrice with 100 ml saturated NaHCO$_3$. The aqueous phase was acidified with 3N HCl and extracted with DCM. The organic layer dried over Na$_2$SO$_4$ and concentrated totally under vacuum, 40° C., to afford the title compound as a white crystalline solid, 9.6g, yield 80%.

Measurements of the produced B2 were as follows: $^1$H-NMR (400 MHz, CDCl$_3$), δ0.92–1.01 (m, 12H), 2.29 (m, 2H), 4.23 (m, 1H), 4.38–4.45 (m, 3H), 4.93 (d, 1H), 5.34 (d, 1H), 7.29–7.77 (Ar, 8H). $^{13}$C-NMR (400 MHz, CDCl$_3$), δ17.0, 17.4, 18.9, 19.1 (CH$_3$), 30.0, 31.1 (CH), 47.1 (CH), 59.2 (CH$_2$), 67.2 (CH), 120.0, 124.0, 125.1, 127.0, 127.7, 141.7, 143.7 (Ar), 156.4, 171.7, 173.8 (C=O).

Also, for the produced B2, MS-EIS 462.4 (M+Na$^+$), 478.2 (M+K$^+$).

Synthesis of the Acyclic Depsipeptide (D1):

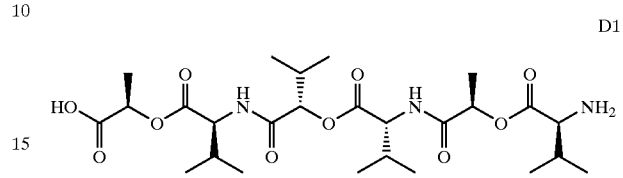

D1

Solid phase synthesis was carried out on 2.9 g of Wang resin (1.1 mmol/g). The resin was prepared by adding 20 ml of DMF and mixing for 30 min with N$_2$ at which point the DMF was removed by filtration. During which time, 2.5 eq. (3.28 g) to resin loading of B1 was dissolved in 50 ml of DCM to which 1.25 ml diisopropylcarbodiimide was added. This was stirred for 25 min. at which point the DCM was removed under vacuum, 40° C. 10 ml of DMF was added to the dried residue and was subsequently added to the swelled resin. 0.1 eq (40 mg) of 4-dimethylaminopyridine was also added and the mixture was mixed with N$_2$ for 1 hr. The reaction solution was filtered off and the resin was washed thrice with 20 ml DMF, thrice with 20 ml MeOH and dried under vacuum. Loading was tested by cleaving the fmoc protection group from a known mass of resin (20 mg) with 20% piperidine in DMF and monitoring the UV absorption at 290 nm. Using a molar extinction coefficient value of 4950 a loading of 50% was obtained. The process was repeated in full to obtain 70% loading.

The remaining resin was deprotected with 20% piperidine in DMF (30 ml, 10 min.). The solution was filtered off and the resin was washed thrice with 20 ml DMF, thrice with 20 ml MeOH, thrice with 20 ml DMF. B2 was added at 2.5 eq. (3.50 g) to 30 ml of DMF and 4.15 g (2.5 eq.) of PyBOP, 1.08 g (2.5 eq.) HOBT, and 0.278 ml (5 eq.) of diisopropylethylamine. This mixture was then added to the resin and mixed with N$_2$ for 4 hr. The solution was filtered off and the resin was washed thrice with 20 ml DMF, thrice with 20 ml MeOH, once with EtOH and dried under vacuum. Complete coupling was confirmed by the Kaiser test for free amine.

The general procedure was repeated again for the addition of the final block, B1. The linear depsipeptide was cleaved from the dried resin with TFA/H$_2$O/TIS 95/2.5/2.5 over 2 hr. by mixing with N$_2$. The cleavage mixture was filtered off and concentrated totally. The brown residue was dissolved and concentrated twice more with toluene. The crude product was purified by flash chromatography (Biotage Flash40 column 15 cm×7 cm, DCM/MeOH 95/5) to obtain 380 mg of off white powder.

Measurements of the produced D1 were as follows: $^1$H-NMR (400 MHz, DMSO-d$_6$), inter alia δ0.72–84 (m, 24H), 1.21–1.26 (m, 6H), 1.96–2.00 (m, 4H).

Also, for the produced D1, MS-EIS 560.4 (M+H$^+$), 582.4 (M+Na$^+$).

Synthesis of 1:

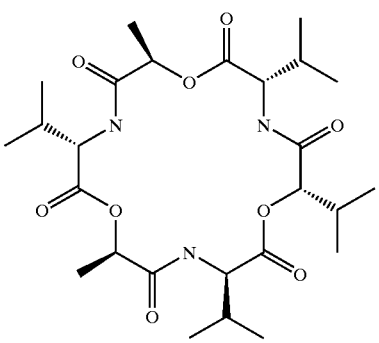

150 mg (0.276 mmol) of the acyclic depsipeptide (D1) was dissolved into 20 ml thionyl chloride and mixed for 1.5 hr, at which point the solution was concentrated totally to give a white solid. The residue was immediately taken up in 150 ml anhydrous benzene and 0.144 ml (1.05 mmol) triethylamine and mixed for 18 hr. The solvent was removed under vacuum, 40° C. The residue was taken up in 100 ml DCM and washed with 100 ml 10% citric acid, 100 ml saturated $NaHCO_3$, dried over $Na_2SO_4$ and the organic layer concentrated totally to afford 75 mg of an off white powder of title compound 1, yield 50%.

For the produced 1, MS-EIS 542.6 ($M+H^+$), 564.4 ($M+Na^+$), 580.4 ($M+K^+$).

EXAMPLE 2
Compound of the Invention in an Ion Selective Electrode (ISE)

Testing of an ionophore in an ISE is well known in the art and may take many forms see, e.g. *Ion Selective Electrode Methodology*, Vol. 1, Covington, A. K., ed., (CRC Press, Inc., 1979) pp. 32–33, incorporated herein by reference. A particular convenient method is in a planar format (U.S. Pat. No. 5,554,272, for example). We tested compound 1 in such a format.

We constructed three sensors in the planar format as in U.S. Pat. No. 5,554,272, using an internal electrolyte polymeric layer (see also, U.S. Pat. Nos. 5,911,862 and 5,804,049). The ion selective membrane was composed of 30 wt % polyvinyl chloride, 69 wt % dioctyl phthalate and 1 wt % of compound 1. The membrane could also contain a lipophilic salt, e.g. potassium-tetra-(p-chloro-phenyl)-borate, but these chemicals are not required.

The sensors were tested using solutions containing $NH_4Cl$ (0.5–100 mM), 100 mM Tris buffer and 0.05 g/l Brij 700. The output of the sensors, measured in mV, was plotted with respect to time (see, FIG. 1). Where 1=0.05 mM, 2=1 mM, 3=5 mM, 4=10 mM, 5=50 mM, 6=100 mM $NH_4Cl$ respectively and A, B, C are sensor #1, 2, 3 respectively.

The slopes and linearity of the sensors are shown in TABLE 1.

TABLE 1

|  | Sensor #1 | Sensor #2 | Sensor #3 |
| --- | --- | --- | --- |
| Slope (mV/dec) | 56.4 | 57.4 | 56.5 |
| $R^2$ | 0.9991 | 0.9990 | 0.9990 |

The selectivities ($logK_{a/j}^{POT}$) of the sensors were determined by the fixed interference method (Frant MS et al. *Pure Appl. Chem.* 48, 127 (1976)) with respect to potassium and sodium,

TABLE 2

| Sensor | $logK_{a/j}^{POT}$ j = Potassium | $logK_{a/j}^{POT}$ j = Sodium |
| --- | --- | --- |
| 1 | −.2 | −1.5 |
| 2 | −.2 | −1.5 |
| 3 | −.2 | −1.5 |

In summary, the data presented in this EXAMPLE shows that indeed that the compound of the invention functions as an ammonium ionophore and can be used within an ion selective electrode to measure the concentration of ammonium ions.

The foregoing description has been presented only for the purposes of illustration and is not intended to limit the invention to the precise form disclosed, but by the claims appended hereto.

We claim:
1. A compound, having the structure:

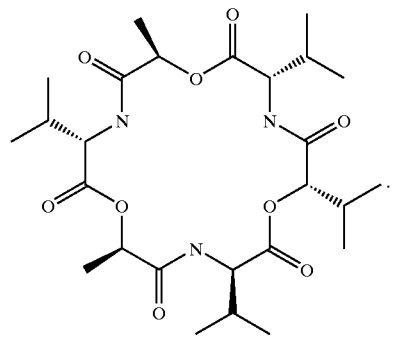

2. A method of making a compound having the structure:

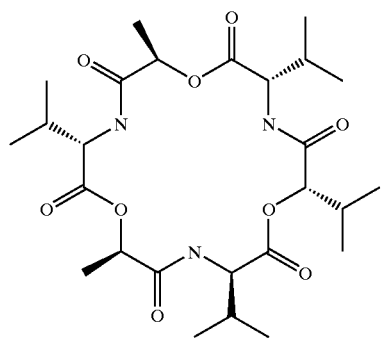

comprising the steps of:

(a) obtaining a compound having the structure:

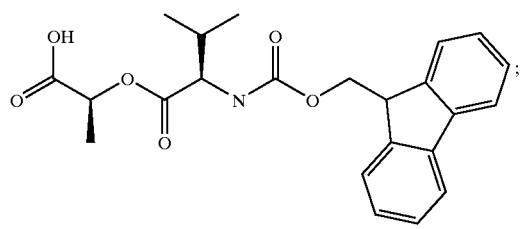

(b) obtaining a compound having the structure:

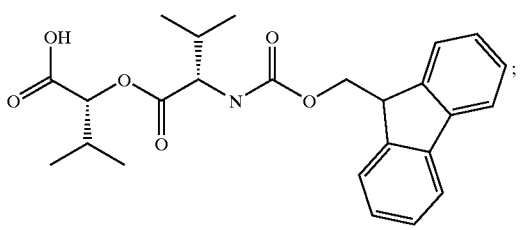

(c) synthesizing an acyclic depsipeptide from the compounds obtained in step (a) and step (b); and
(d) synthesizing the compound having the structure:

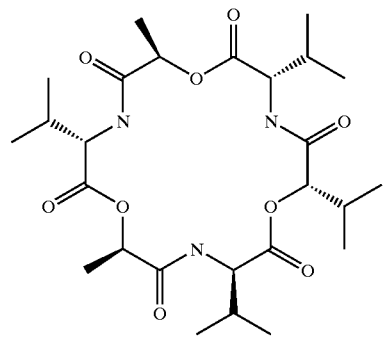

from the acyclic depsipeptide of step (c).

3. An ammonium ion selective matrix, comprising:
(a) an ionophore having the structure:

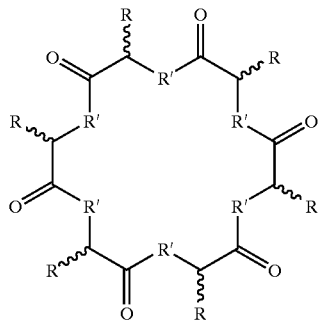

wherein
(i) wherein R is a chemical group selected from the set consisting of hydrogen and alkyl, alkoxyalkyl, alkoxyacyl, alkylamino, alkylnitroso, alkylcyano, alkylthio, alkylsulfinyl, alkylsulfonyl, alkenyl, alkoxyalkenyl, alkenylacyl, alkenylamino, alkenylnitroso, alkenylcyano, alkenylthio, alkenylsulfinyl, alkylsulfonyl, alkynyl, alkoxyalkynyl, alkynylacyl, alkynylamino, alkynylnitroso, alkynylcyano, alkynylthio, alkynylsulfinyl, and alkynylsulfonyl and substituted or unsubstituted aryl groups with or with out heteroatoms, and
(ii) R' is either nitrogen or oxygen; and
(b) an ammonium ion permeable matrix material in which the ionophore is situated, wherein the matrix is adapted for use in an ion selective electrode.

4. The ammonium ion selective matrix of claim 3, wherein the matrix material comprises a glass or a polymer.

5. A method for detecting the presence of ammonium ions in a fluid sample, comprising the steps of:
(a) obtaining a matrix comprising an ionophore having the structure:

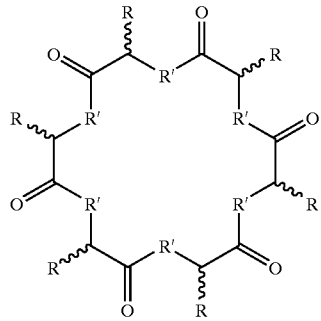

wherein
(i) wherein R is a chemical group selected from the set consisting of hydrogen and alkyl, alkoxyalkyl, alkoxyacyl, alkylamino, alkylnitroso, alkylcyano, alkylthio, alkylsulfinyl, alkylsulfonyl, alkenyl, alkoxyalkenyl, alkenylacyl, alkenylamino, alkenylnitroso, alkenylcyano, alkenylthio, alkenylsulfinyl, alkylsulfonyl, alkynyl, alkoxyalkynyl, alkynylacyl, alkynylamino, alkynylnitroso, alkynylcyano, alkynylthio, alkynylsulfinyl, and alkynylsulfonyl and substituted or unsubstituted aryl groups, with or without heteroatoms group, and
(ii) R' is either nitrogen or oxygen; wherein the matrix is adapted for use in an ion selective electrode;
(b) connecting the matrix with a sensing instrument;
(c) providing an electrical signal, potential or current, to the sensing instrument through the matrix;
(d) contacting the fluid sample with the matrix; and
(e) measuring an electrical signal provided by the sensing instrument; wherein the electrical signal can be correlated with the activity of ammonium ions in the fluid sample.

6. An ammonium ion-selective sensor, comprising an ammonium ion permeable matrix material, wherein the matrix is adapted for use in an ion selective electrode, wherein the matrix comprises an ionophore having the structure:

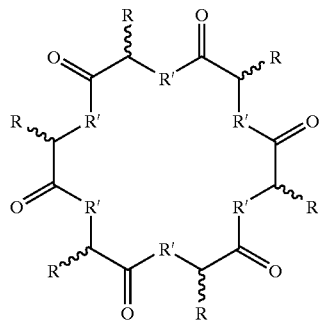

wherein
(a) R is a chemical group selected from the set consisting of hydrogen and alkyl, alkoxyalkyl, alkoxyacyl, alkylamino, alkylnitroso, alkylcyano, alkylthio, alkylsulfinyl, alkylsulfonyl, alkenyl, alkoxyalkenyl, alkenylacyl, alkenylamino, alkenylnitroso, alkenylcyano, alkenylthio, alkenylsulfinyl, alkylsulfonyl, alkynyl, alkoxyalkynyl, alkynylacyl, alkynylamino, alkynylnitroso, alkynylcyano, alkynylthio, alkynylsulfinyl, and alkynylsulfonyl and substituted or unsubstituted aryl groups, with or without heteroatoms, and (b) R' is either nitrogen or oxygen.

7. The sensor of claim 6, wherein the matrix material comprises a glass or a polymer.

8. The sensor of claim 6, wherein the matrix material further comprises an ionic additive.

9. The sensor of claim 6, wherein matrix material is connected with a sensing instrument.

10. The sensor of claim 6, further comprising a reference electrode.

11. The sensor of claim 6, wherein the ionophore has the structure:

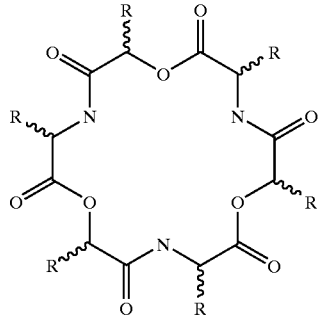

wherein R is a chemical group selected from the set consisting of hydrogen and alkyl, alkoxyalkyl, alkoxyacyl, alkylamino, alkylnitroso, alkylcyano, alkylthio, alkylsulfinyl, alkylsulfonyl, alkenyl, alkoxyalkenyl, alkenylacyl, alkenylamino, alkenylnitroso, alkenylcyano, alkenylthio, alkenylsulfinyl, alkylsulfonyl, alkynyl, alkoxyalkynyl, alkynylacyl, alkynylamino, alkynylnitroso, alkynylsulfonyl, alkynylcyano, alkynylthio, alkynylsulfinyl, and alkynylsulfonyl and substituted or unsubstituted aryl groups, with or without heteroatoms.

12. An ammonium ion-selective sensor, comprising an ammonium ion permeable matrix material comprising an ionophore having the structure:

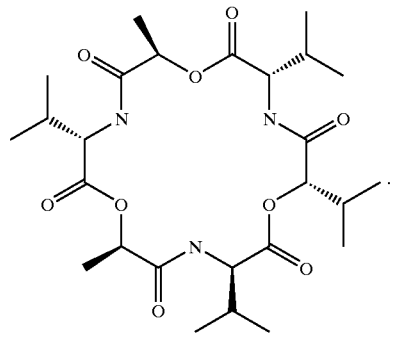

* * * * *